US008831538B2

(12) United States Patent
Yuen

(10) Patent No.: US 8,831,538 B2
(45) Date of Patent: Sep. 9, 2014

(54) PERFORMANCE MONITORING APPARATUS AND CASING THEREFOR

(75) Inventor: Paul Anthony Yuen, Hong Kong (CN)

(73) Assignee: Dayton Technologies Limited, New Territories (HK)

( * ) Notice: Subject to any disclaimer, the term of this patent is extended or adjusted under 35 U.S.C. 154(b) by 53 days.

(21) Appl. No.: 13/499,334

(22) PCT Filed: Sep. 30, 2010

(86) PCT No.: PCT/IB2010/054421
§ 371 (c)(1),
(2), (4) Date: Jun. 14, 2012

(87) PCT Pub. No.: WO2011/039723
PCT Pub. Date: Apr. 7, 2011

(65) Prior Publication Data
US 2012/0252544 A1 Oct. 4, 2012

(30) Foreign Application Priority Data

Sep. 30, 2009 (HK) .................................. 09109094.7

(51) Int. Cl.
H04B 1/38 (2006.01)
(52) U.S. Cl.
USPC .......................... 455/90.1; 455/557; 455/556.1
(58) Field of Classification Search
USPC ..................... 455/556.1, 557, 575.1–575.9, 455/90.1–90.3
See application file for complete search history.

(56) References Cited

U.S. PATENT DOCUMENTS

| 6,002,982 A | 12/1999 | Fry | |
|---|---|---|---|
| 6,013,007 A * | 1/2000 | Root et al. | 482/8 |
| 7,265,723 B1 | 9/2007 | Chan et al. | |
| 2007/0021269 A1 | 1/2007 | Shum | |
| 2007/0184781 A1 * | 8/2007 | Huskinson | 455/42 |
| 2007/0233395 A1 * | 10/2007 | Neel et al. | 702/19 |
| 2008/0053852 A1 | 3/2008 | Ko et al. | |

FOREIGN PATENT DOCUMENTS

CN 101137276 A 3/2008
WO WO 01/00281 A2 1/2001

OTHER PUBLICATIONS

International Search Report (PCT/ISA/210) issued on Feb. 17, 2011, by Chinese Patent Office as the International Searching Authority for International Application No. PCT/IB2010/054421.

* cited by examiner

Primary Examiner — Christian Hannon
(74) Attorney, Agent, or Firm — Buchanan Ingersoll & Rooney PC

(57) ABSTRACT

A performance monitoring apparatus comprising an assembly of a performance monitoring module and a general purpose portable telecommunications device such as a mobile telephone or mobile smart phone connected for data communication mounted on a common casing. The performance monitoring module is adapted for receiving performance signals from at least one performance sensor and for converting the performance signals into performance data. The general purpose portable telecommunications device is configured to be activate-able to cause the performance monitoring module to transfer performance data to the general purpose portable telecommunications device. The common casing comprises mounting means for mounting onto a support surface. This module is adapted for cooperative operation with a general purpose portable telecommunications device to expand its processing and display power while maintaining a low cost simple design and compactness.

13 Claims, 14 Drawing Sheets

PERFORMANCE MONITORING APPARATUS AND CASING THEREFOR

FIELD OF THE INVENTION

The present invention relates to performance monitoring apparatus, and more particularly to portable or mobile sports performance monitoring apparatus, such as bicycle computers, runner's computers, swimmer's computers and the like. More specifically, although not solely limited thereto, the present invention relates to bicycle computer apparatus.

BACKGROUND OF THE INVENTION

A performance monitoring apparatus, also known as a 'sports performance monitoring apparatus', 'sports monitor' or 'sports computer' in short, is typically configured to collect performance and/or physiological data of a person while doing sports or other physical exercises, and to analyze the collected data to provide feedback information to a user. Typical feedback information usually includes performance indicators and/or physiological conditions of a user. Typically collected performance indicators include, for example, physical performance data such as running speed, acceleration, step width, and running cadence in the case of a runner's computer; cycling speed, cycling cadence, and cycling power in the case of a bicycle computer; stroke count, stroke time, stroke count per lap, swimming speed, and stroke span in the case of a swimmer's computer.

Typically collected physiological data include, for example, heart-rate, electrocardiogram ("ECG") signals, blood pressure, blood sugar, blood oxygen level of a sportsperson when performing physical exercise. The collected data may be used for analyzing the physical performance characteristics of a sportsperson to tailor make training programs, to evaluate the strength and weakness, to understand the physiological behaviors, patterns, and/or to evaluate or extrapolate the physiological and performance limits of the sportsperson.

In order to provide more comprehensive information for evaluation, extrapolation and correlation, sports monitors may also include peripheral accessories such as barometer, compass, humidity meter, tilt meter, wind meter, GPS, etc to provide environmental or geographic information.

Mobile sports monitors are usually carried by a sportsperson either on the body or on a moving object powered by the sportsperson. As such, they are compact and lightweight in order to minimize the deadweight and motion resistance. For example, a typically good bicycle computer would weigh less than 80 grams and occupies less than 30 cm$^3$, which is of about bite-size.

Due to these general constraints, a mobile sports monitor is usually equipped with only minimum or essential components necessary to perform the minimum specific functionality, and do not provide other useful or cosmetic functions. For example, a typical mobile performance monitor usually only includes a basic micro-controller with built-in memory for data logging and display. The logged data are usually overwritten when new data are logged, as the available memory space is severely limited. The micro-controller is only a simple micro-processor programmed with basic functions for power saving, and the display is typically a monochrome dot-matrix LCD display adapted primarily for simple textual display. However, such minimum functionality may not meet the requirements of the more sophisticated sportspersons or their support team such as the coach or crew members. For example, a sports monitor with a small memory could not store and log enough data for comprehensive sports performance profile analysis. Yet, a substantial increase in memory space and processing power would have a consequence of a more bulky monitor, a more powerful processor, a more powerful battery and a more expensive device.

In light of the above, it would be appreciated that traditional sports monitors are always a product of compromise which is adapted to strike a balance among costs, compactness and performance.

Furthermore, a sports computer is typically customized for operation with a designated sensor for detecting the characteristic motion of a specific sport. As such, different sports computers will have to be used for different sports and this means a sports person will have to carry several bulky and expensive sports computers if high performance sports computers are required.

Therefore, it would be advantageous if there could be provided sports monitors that would mitigate the functionality limitations of conventional apparatus while maintaining the advantages of a special purpose device, such as low cost, low-weight, easy to use and compact.

SUMMARY OF INVENTION

According to the present invention, there is provided a performance monitoring apparatus comprising an assembly of a performance monitoring module and a general purpose portable telecommunications device such as a mobile telephone or mobile smart phone connected for data communication, wherein the performance monitoring module is adapted for receiving performance signals from at least one performance sensor and for converting the performance signals into performance data, wherein the general purpose portable telecommunications device is configured to be activateable to cause the performance monitoring module to transfer performance data to the general purpose portable telecommunications device; and wherein the common casing comprises mounting means, such as a mounting means for mounting onto a bicycle, a sports equipment, or a user.

With the built-in data communication capability connected to the processor, the performance monitor module could tap into and utilize a vast pool of resources of a much more powerful general purpose portable telecommunications device, such as a netbook computer, a mobile telephone or a mobile smart phone such as i-phone® or i-pod®, or a superphone. For example, by tapping into the processing power of a general purpose portable telecommunications device, which is typically equipped with a 32- or 64-bit high speed microprocessor such as ARM's® Cortex-A8 processor commonly used in smart phones, a much more powerful and versatile portable performance monitoring apparatus is readily available to a user by utilizing a simple, compact and low-cost purpose-built monitoring module without the need to purchase an expensive, powerful but bulky designated monitoring apparatus for each specific purpose. Such a purpose-built monitoring module is advantageous because a user can select a portable monitoring module designed for a specific purpose for cooperative use a general purpose mobile telecommunications device and by activating a customized application program. As such, a single mobile telecommunications device could be readily configured into a variety of performance monitoring apparatus at minimal costs. The use of a general purpose mobile telecommunications is particularly advantageous because new versions of application programs could be readily download.

In an embodiment, the performance monitoring apparatus comprises a main casing, the main casing including mounting means for securing onto a user or a bicycle and a receptacle for securely receiving the performance monitoring module and the portable telecommunications device in mated connection.

The performance monitoring module may comprise a display for displaying performance data and a toggle switch, wherein the type of performance data to be instantaneously displayed is selectable by a user upon toggling of the toggle switch.

The common casing may comprise a first receptacle for receiving the performance monitoring module and a second receptacle for receiving the portable telecommunications device, and the first and second receptacles are in communication via an inter-receptacle aperture defined by a bridge member on the common casing; and wherein the bridge member is arranged also to latch the assembly of the performance monitoring module and the general purpose portable telecommunications device on the common casing. A performance apparatus comprising such a casing provides a robust arrangement for harsh operating conditions.

The performance monitoring module may comprise a protruding mechanical adapter for making mating connection with the portable telecommunications device, and wherein the mechanical adapter extends through the inter-receptacle aperture when the performance monitoring module is seated in the first receptacle. The mating connection arrangement provides a simple yet reliable attachment means which is easy to attach and detach.

The protruding mechanical adapter may be received in the inter-receptacle aperture in a closely-fitted manner. Such an arrangement provides a simple yet reliable latching mechanism for keeping the assembly of the smart phone and the performance monitoring module intact within the casing.

The common casing may further comprise a resilient adapter seat which is shaped to squarely seat the portable telecommunication device in the second receptacle. Such an adapter facilitates change of smart phones more easily at the discretion of a user.

The adapter seat may be detachable so that different adapters are usable for seating different models of portable telecommunications devices in the second receptacle.

The performance monitoring module may be adapted for receiving performance signals from at least one performance sensor and for converting the performance signals into performance data, wherein the general purpose portable telecommunications device is configured to be activate-able to cause the performance monitoring module to transfer performance data to the general purpose portable telecommunications device; characterized in that the portable casing comprises a bicycle mounting means for mounting onto a bicycle.

These and other features of the invention will be explained in further detail below.

BRIEF DESCRIPTION OF THE DRAWINGS

Exemplary embodiments of the present invention will be explained below by way of example and with reference to the accompanying drawings, in which.

DETAILED DESCRIPTION OF EXEMPLARY EMBODIMENTS

Figure 1:
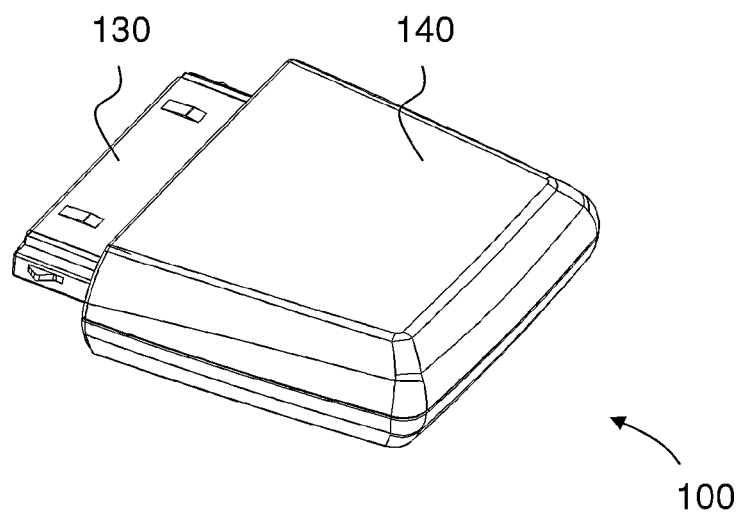
FIGS. 1 and 1A respectively depict perspective views from above and below of a bicycle computer module according to an embodiment of the present invention.
Figure 1A:
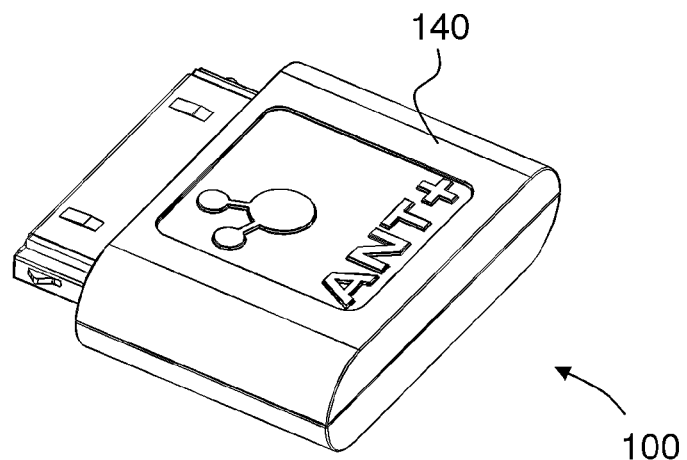
Figure 2:
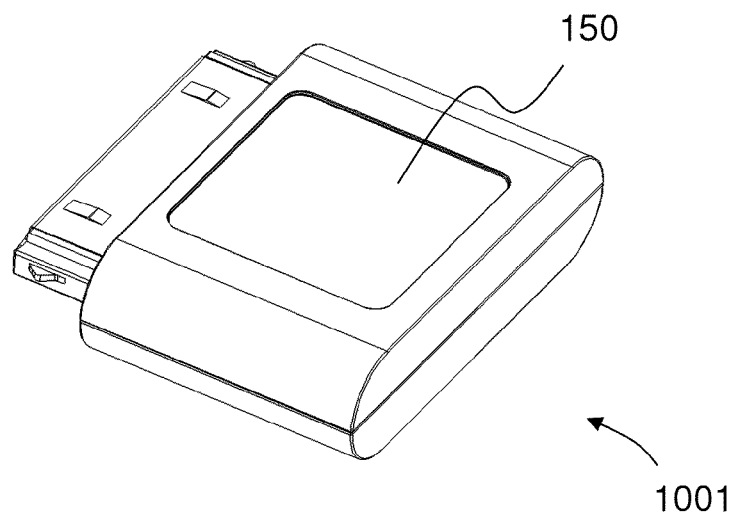
FIGS. 2 and 2A depict a top perspective view of a bicycle computer module according respectively to a second and a third embodiment of the present invention.
Figure 2A:
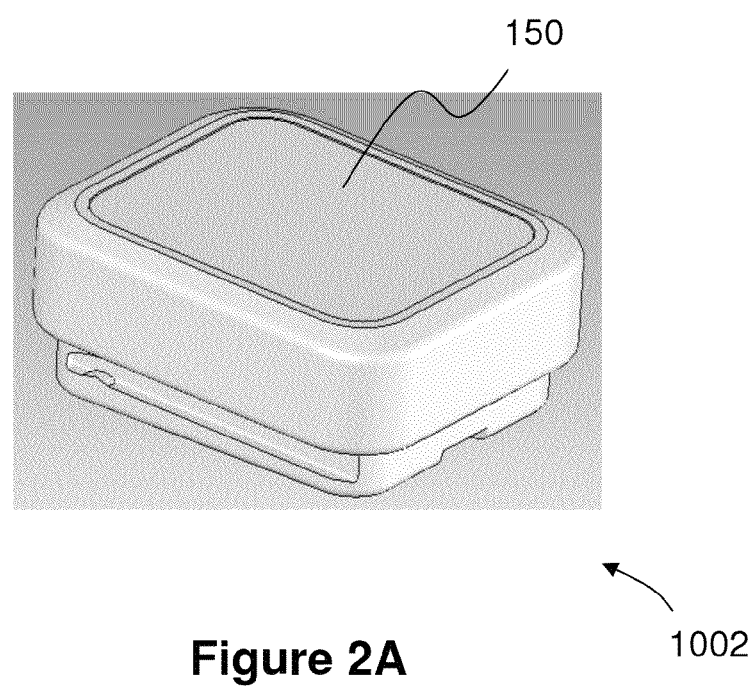
Figure 3:
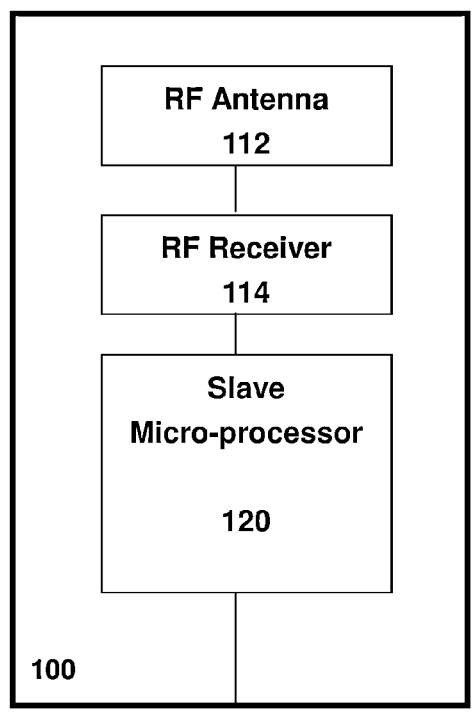
FIG. 3 is basic schematic circuit block diagram of the bicycle computer dongle of FIGS. 1 and 2.

A bicycle computer module (nicked named 'bicycle computer dongle') 100 of FIGS. 1 to 5 as an example of a performance monitoring module of the present invention comprises a signal receiver 110, a micro-processor 120 and an adapter 130 which are housed within a rigid and moulded plastic housing 140. The signal receiver 110 comprises an antenna 112 for receiving radio frequency (RF) signals and an RF receiver 114 for frontend processing of RF signals received by the antenna and forwarding to the microprocessor 120.

The signal receiver is adapted to receive bicycle performance signals from bicycle performance sensors operating at 2.4 GHz using ANT® or ANT+® protocols and the received bicycle performance signals are processed by the microprocessor for output as bicycle performance data. The dongle is adapted to process common performance data such as speed, cadence and power, and the sensors therefore include respectively speed, cadence and power sensors.

The micro-processor 120 is a low-end 4 bit or 8-bit microprocessor which is pre-programmed to process bicycle performance signals received by the RF receiver and convert the received signals into performance data according to established methodology. The signal processing algorithms are pre-stored in the memory of the microprocessor, which also includes additional memory space for saving and logging performance data.

The adapter 130 is formed as a protrusion extending from the front end of the dongle, and is adapted for mating connection with a smart phone for applications to be described below. In addition, locking means are provided on the adapter to secure latching of the dongle onto a smart phone.

The dongle is of about bite size, measuring less than 5 cm long, 5 cm wide and 1 cm high, and weighs less than 80 gram. Because of such compactness and lightness, the dongle could be readily stored in a pocket of a user.

Figure 4:
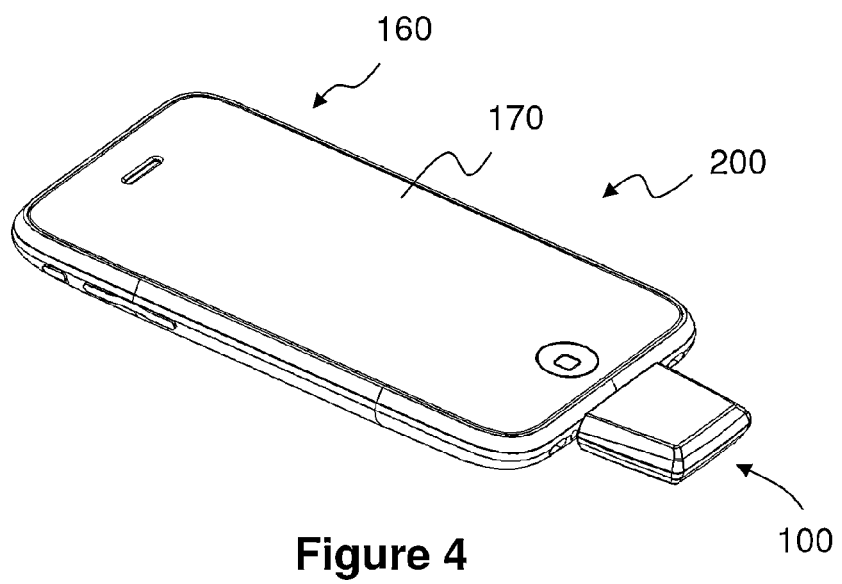
FIG. 4 is a perspective view depicting an exemplary embodiment of a bicycle computer apparatus of the present invention comprising the bicycle computer module of FIGS. 1 and 2 assembled with a smart mobile phone.

FIG. 4 depicts a bicycle computer 200 comprising an assembly of the dongle 100 and a smart mobile phone 160 in mating connection as an example of a bicycle computer apparatus of the present invention. The smart phone comprises a display screen 170, such as an LCD touch screen mounted on a plastic moulded housing, and other components of a typical smart phone such as an i-pod® or an i-phone® of Apple, Inc. The smart phone is installable with software such as application programs and operable by touching on the touch screen, features which are common in most available smart phones. The smart phone is provided with an input/output (I/O) port which is mechanically compatible with the adapter such that the dongle is detachably attachable to the smart phone.

Figure 5:
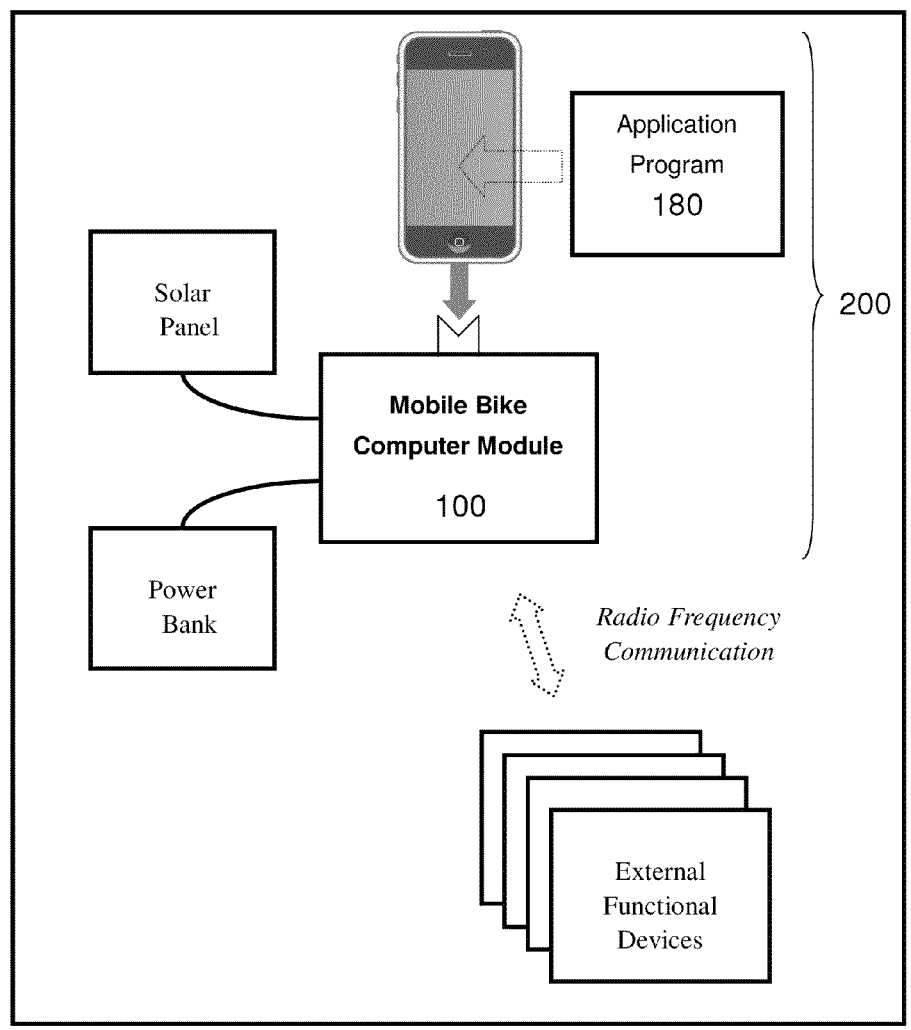
FIG. 5 is a schematic block diagram depicting exemplary functional blocks of the bicycle computer apparatus of FIG. 4.
Figure 6:
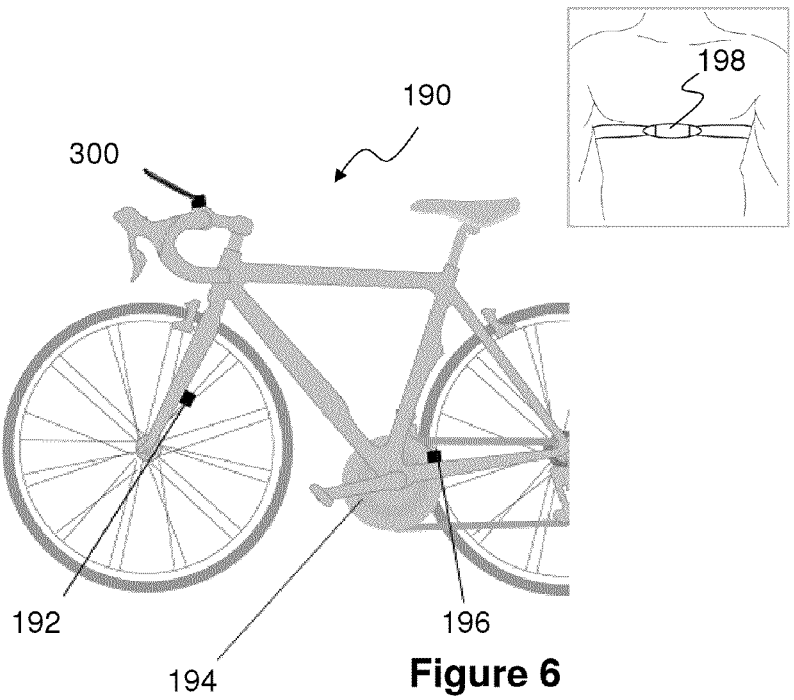
FIG. 6 depicts an exemplary use of the bicycle computer apparatus of FIG. 4 mounted as a bicycle computer pack on a bicycle.

Referring to FIG. 5, the smart phone is installed with application programs 180 for processing performance data collected by the dongle 100, and the dongle is operatively communicable with bicycle performance sensors or other external functional devices, such as solar panels or a power bank for powering the smart phone and/or the dongle, or physiological sensors such as ECG sensors, heart rate sensors, or blood sugar sensors. As shown in FIGS. 5 & 6, the physiological sensors are operatively connected to the dongle by a wireless link for convenience.

In use, the bicycle computer 200 is mounted as a single bicycle computer pack 300 on the front handle bar of a bicycle, as shown in FIG. 6. To detect performance parameters, a speed sensor 192, a power sensor 194, and a cadence sensor 196, a heart-rate sensor 198 are mounted on the bicycle and in wireless communication with the dongle installed on the bicycle computer pack. The bicycle computer pack 300 includes a bicycle computer 200 and a casing 380 including a receptacle for receiving the bicycle computer 200. The casing 380 comprises a hinged compartment defining the receptacle and includes a bicycle mount 350 for securing onto the bicycle frame. The inclination of the bicycle mount is adjustable to fit the personal preference of a rider for a comfortable view of information being displayed on the screen 170. When a rider has to leave the bicycle unattended, the rider may detach the pack 300 from the bicycle frame, or only removes the more valuable smart phone and dongle while leaving the casing attached to the bicycle.

Figure 9:
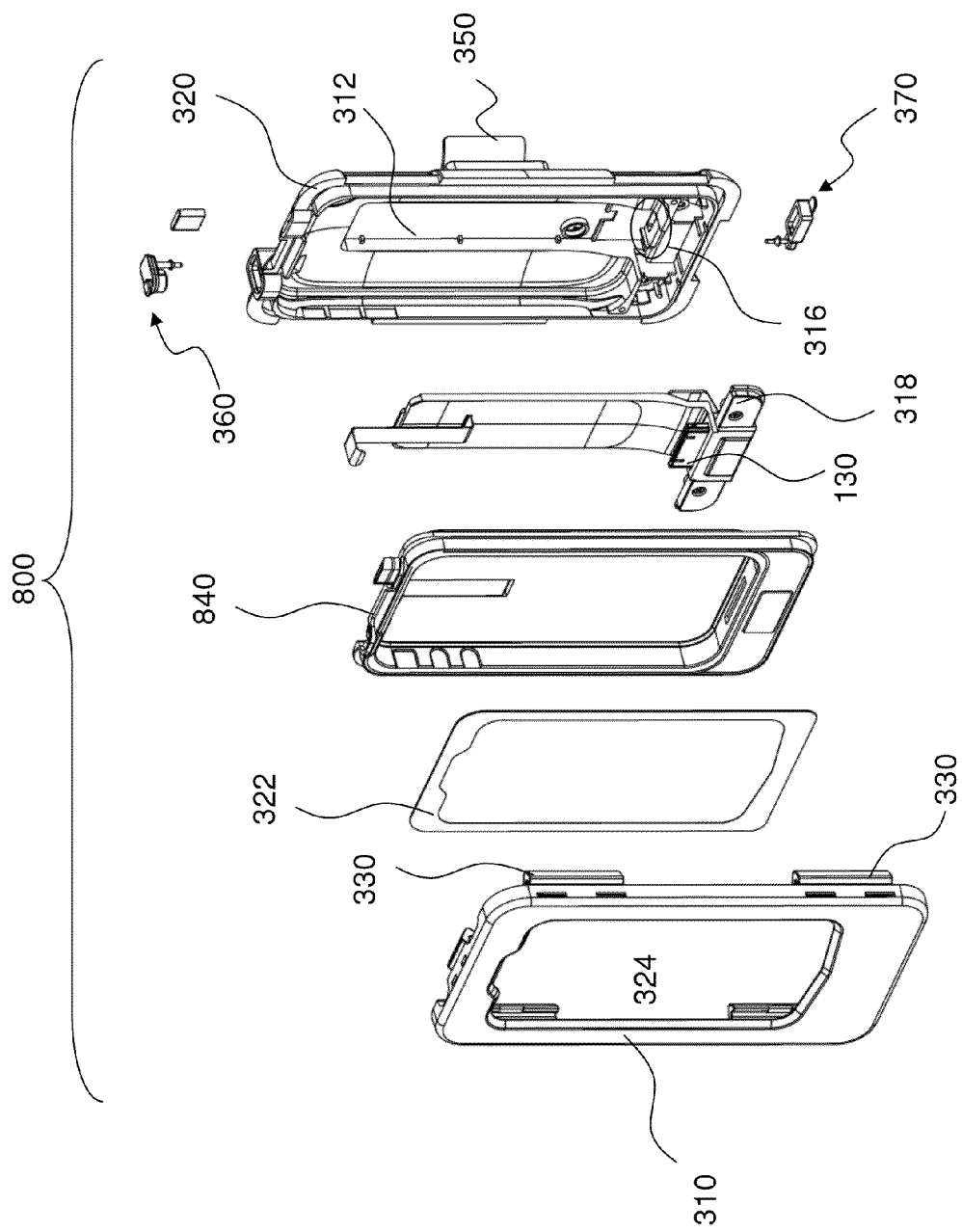
FIGS. 9 is an exploded view of a second bicycle computer assembly according to another embodiment of the present invention.

Because of the large processing power and memory of the smart phone, the bicycle computer is now configurable to process more varieties of signals, even though it has a relatively low-end processor and small memory. To capitalize on the versatility of this bicycle computer arrangement of the present invention, a bicycle computer dongle 400 with more complicated functionality as depicted in the block diagram of FIG. 9 is provided.

This bicycle computer dongle 400 is built on a relatively low-end and low-speed processor having a small built-in memory, but is programmed to cooperate with many varieties of sensors to meet the requirements of the more sophisticated users. More particularly, the dongle 400 is pre-arranged to operate with a combination of sensors for detecting environment parameters such as pressure, humidity, temperature, altitude, path or route, and/or distance-to-target; or physiological parameters such as blood pressure, blood oxygen, and/or body temperature.

Figure 8:
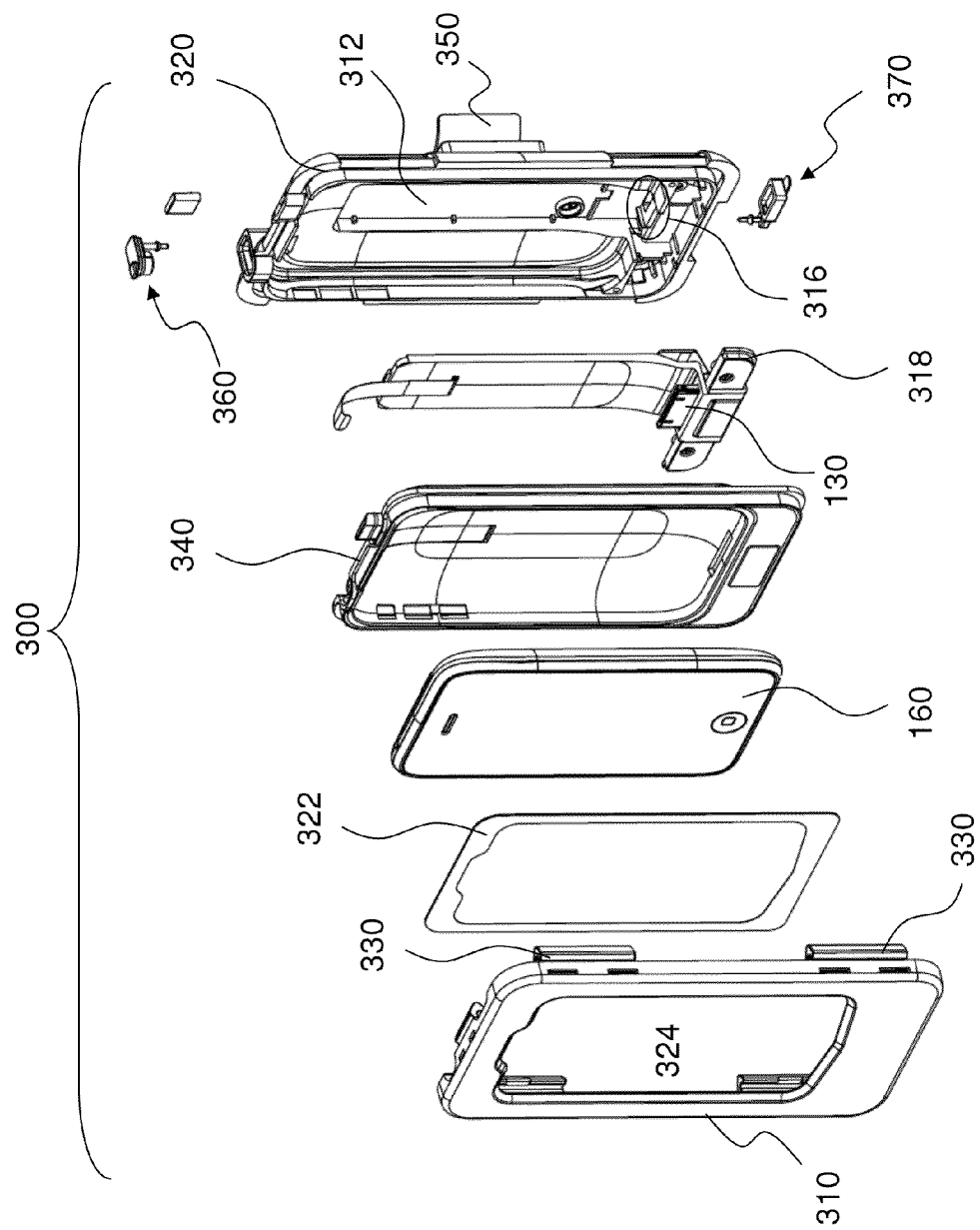
FIG. 8 is a further exploded view of the bicycle computer pack of FIG. 6, FIGS. 8A and 8B are respectively top and bottom perspective views of the assembly of FIG. 8, FIGS. 8C and 8D are respectively the internal views of the first and second casing parts of FIGS. 8A and 8B, FIGS. 8E and 8F are enlarged views of the sealing parts of the casing of FIG. 8.
Figure 8B:
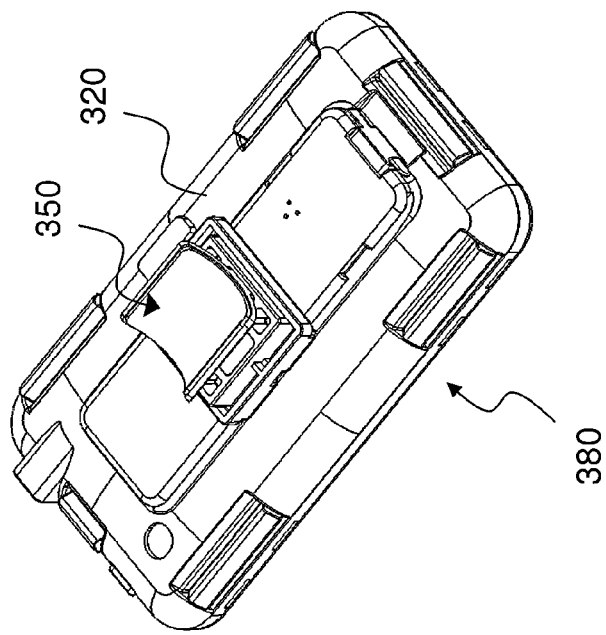
Figure 8A:
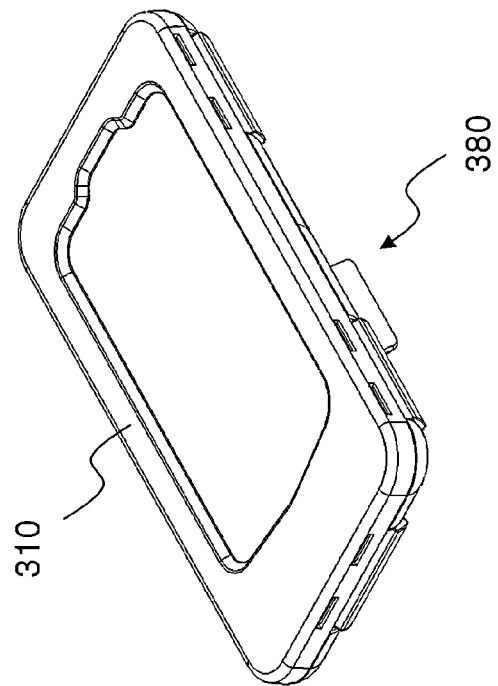

To operate the bicycle computer, a user will firstly plug the dongle 100 into the smart phone 160 to establish a communication link and turn on both devices, as illustrated in FIG. 8. After the initial starting up, the application software will operate and cause the microprocessor of the smart phone to establish a communication link between the smart phone and the RF receiver of the dongle. Next, the microprocessor of the smart phone will search for available sensors via the RF receiver. After the external sensors have been identified, the microprocessor will maintain an RF communication link with the sensors and to receive performance data from the sensors via the dongle. The dongle 100 provides initial performance signal to performance data conversion for onward transmission to the smart phone. Through configuration of the smart phone to cooperate with the specific features of the dongle by utilizing the fast processor and huge memory size of the smart, the bicycle computer 200 has a capability to handle and process signals from multiple sensors, and such a capability is unmatched by other known bicycle computers.

In operation, the microprocessor 120 of the dongle is operated to receive signals detected by the various sensors and to convert the received signals as performance data. In this application, the microprocessor 120 operates as a slave processor in response to instructions of the processor of the smart mobile phone 160. In the course of operation, the collected performance data are transmitted to the smart mobile phone for logging and further processing. Such a bicycle computer arrangement reduces the processing loading on the microprocessor 160 as well as the memory requirements of the dongle 100.

In a first mode of operation, performance data, such as speed, cadence, and/or distance travelled; and/or physiological data are displayed on the screen, and the information being displayed could be changed or selected by a user through tough screen operation.

In a second mode of operation, data collected by the dongle, whether environmental, physiological or otherwise, are processed by the smart phone together or in combination with other data collected by the smart phone to produce useful information. In a first example, the application software is configured to process GPS data collected by the smart phone via the telecommunications network to provide information, such as information on the course or the best course, available courses, expected time to arrive at a target, or expected distance to target; and to display the relevant information on the smart phone screen. In a second example, collected physiological data are processed by the smart phone to provide health information or advice to the rider. For example, the application program may be devised to monitor the body temperature, heart-rate or blood pressure of a rider and advise the rider to vary the speed or cadence in order to keep the body temperature, heart-rate or blood pressure below an acceptable or pre-determined level. In a third example, environmental data collected by the dongle are utilized by the smart phone to provide rider with information relating to anticipated performance of a rider. For example, the application program may be configured to correlate ambient temperature data and/or humidity and/or atmospheric pressure with heart-rate, blood pressure and/or body temperature etc to advise on a cycling pattern, such as the next rest session. In a fourth example, dongle collected data and smart phone collected date are selective used to devise a riding schedule. For example, to adjust a course or to change the speed to avoid lightning, thunderstorm or bad weather; or to select a course to meet a physical training program selected by a user, or to devise a preferred schedule or choice of schedules to avoid overloading a rider.

In a third mode of operation, the application software may be configured to transmit riding information obtained from data collected by the dongle, or data collected by both the dongle and the smart phone, to a remote station via a telecommunications network. The riding information may include, for example, location, rider fitness state, rider behavior, or rider tracking to facilitate remote tracking.

In a fourth mode of operation, the data transmitted to an external remote station may be further processed, and the processed information, which may contain instructions or guidelines, may be transmitted back to the bicycle computer via a telecommunications network.

While the invention has been explained with reference to the above exemplary embodiments, it would be appreciated to persons skilled in the art that the embodiments are only for illustration only and does not intend to limit on the scope of the invention. For example, while four exemplary modes of operation have been described above, many more modes are possible and the use of data or combination of data is without limit. Although the dongle and the sensors are described as linked by 2.4 GHz wireless channel, it would be appreciated that while the selected exemplary frequency channel is good for the purpose, other frequencies could be used and even wire connection could be used between the sensors and the dongle without loss of generality. Also, while the ANT® or ANT+® protocols are mentioned, other protocols could be used when desirable. Furthermore, while a smart phone such as i-pod or an i-phone has been used as an example of a suitable portable telecommunications device, mobile phones such as mobile phones for 2G, 3G or 4G systems are also suitable. In addition, while the dongle and the smart phone in the above exampled are connected in a mechanical mating manner, the dongle and the smart phone need not be mechanically attached and could be connected by wireless protocols such as Bluetooth®. Furthermore while smart phones with a touch screen provides a useful choice, mobile phones with control keypads or other control means such as a toggle switch are equally useful for cooperation with the dongles. While the communication interface of the exemplary dongle is adapted for wired data communication with the mobile phone, it will be appreciated that the data communication could be wireless.

Figure 7:
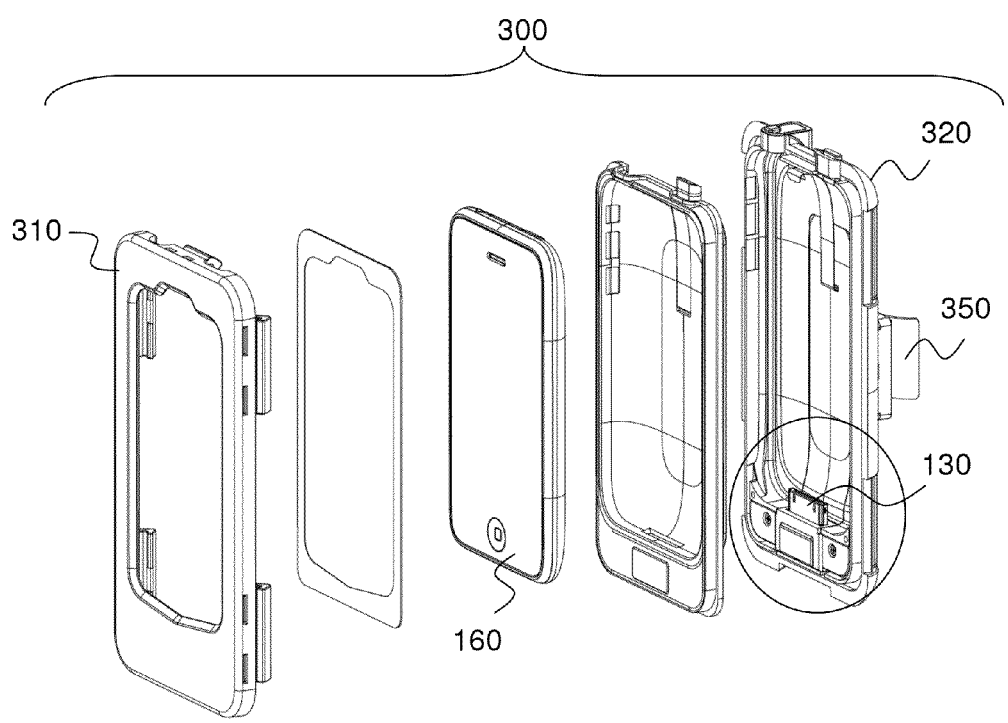
FIG. 7 shows an exploded view of the bicycle computer pack as an example of bicycle computer assembly of FIG. 6.
Figure 7A:
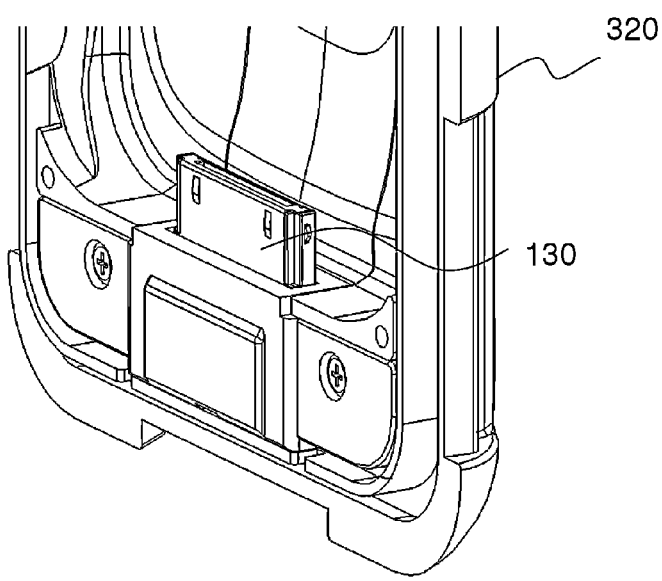
FIG. 7A is an enlarged view of the circled portion of FIG. 7.
Figure 8D:
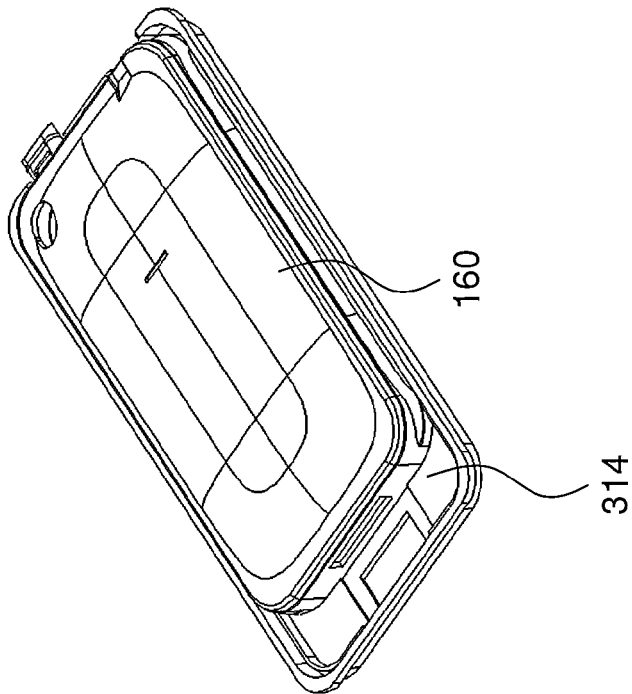
Figure 8C:
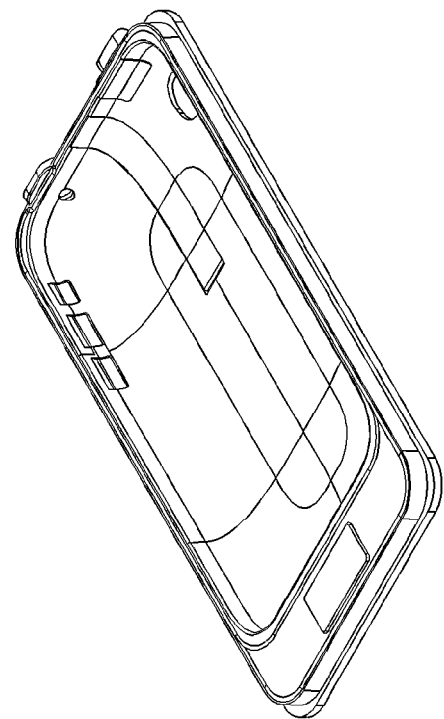

The bicycle computer assembly 300 of FIGS. 7, 8 to 8D as an example of a portable performance monitoring apparatus comprising a bicycle computer module 100 as an example of a performance monitoring module, a smart phone 160 as an example of a general purpose telecommunications device, and a casing 380. The casing 380 comprises an upper casing part 310 and a lower casing part 320 which are detachably attachable by a plurality of clamping clasps. The upper and lower casing parts are arranged to function as a watertight clam shell when closed, and therefore comprises closure means and sealing means. As shown in FIG. 8, a plurality of moveable clasps 330 is distributed around the plurality of the casing 380 and a resilient sealing membrane or a resilient sealing ring 322 as an example of a sealing means is disposed intermediate the smart phone and the upper casing.

The upper casing part comprises a transparent window 324 so that the LCD screen of the smart phone 160 is viewable and the touch screen operable. The lower casing part comprises a first receptacle 312 for receiving the smart phone 160 and a second receptacle 314 for receiving the bicycle computer module. The first 312 and second 314 receptacles are integrally moulded on a plastic shell member of the lower casing 320. The first and second receptacles are in communication, and are communicable through an inter-receptacle aperture 316. The inter-receptacle aperture 316 is defined by a bridge member 318 which partitions the first and second receptacles.

As shown more particularly in FIG. 8, the bridge member 318 is formed as part of a detachable component which is mountable on the lower casing 320. The bridge member 318 and the inter-receptacle aperture are arranged such that the protruding adapter 130 of the bicycle computer module 100 is received within the aperture and latched by the bridge member in a closely fitted manner.

Figure 8F:
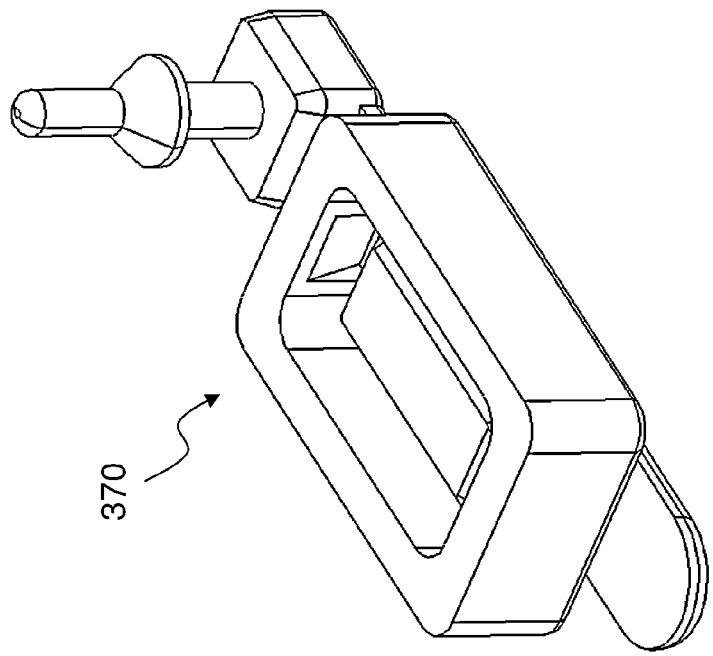
Figure 8E:
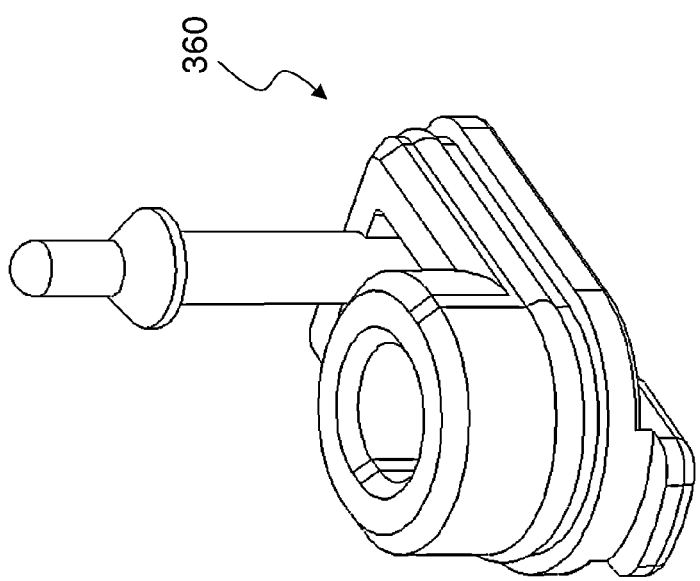

When the smart phone 160 is seated in the first receptacle and mechanically connected with the computer module as an assembly, the assembly will sit squarely on the casing and will be latched in place by the bridge member 318. To promote water tightness, closure taps shown more particularly in FIGS. 8E and 8F for fitting onto the casing are provided.

So that different smart phone models could be accommodated, an adapter pad 340 is provided. This adapter pad 340 is moulded of a resilient material to provide protection to the smart phone, since the operating conditions could be harsh.

To enable the assembly to be securely mounted on a support, such as the handle bar of a bicycle, and to facilitate convenient operation by a user, a mounting clamp or bracket 350 as an example of a mounting means is formed on the bottom side of the lower casing. The mounting bracket 350 also includes means for adjusting the inclination or elevation angle of the assembly with respect to a user.

In use, the assembly is mounted in the casing, and the casing is then closed by operating the clasps, and then mounted on the support. When a user has to leave a bicycle unattended, the user can remove the cased bicycle computer assembly or just removed the more valuable components.

Figure 9B:
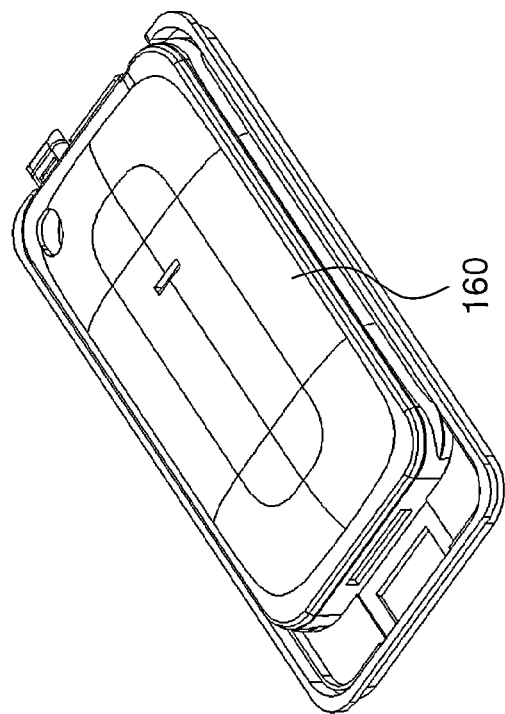
FIGS. 9A and 9B are respectively top and bottom perspective views of the assembly of FIG. 9.
Figure 9A:
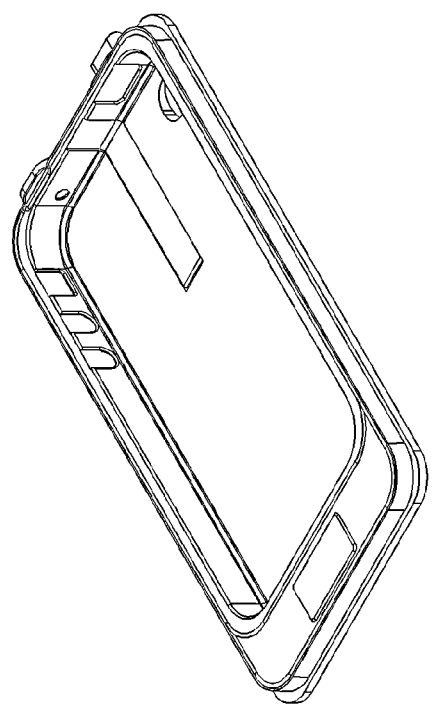
Figure 10:
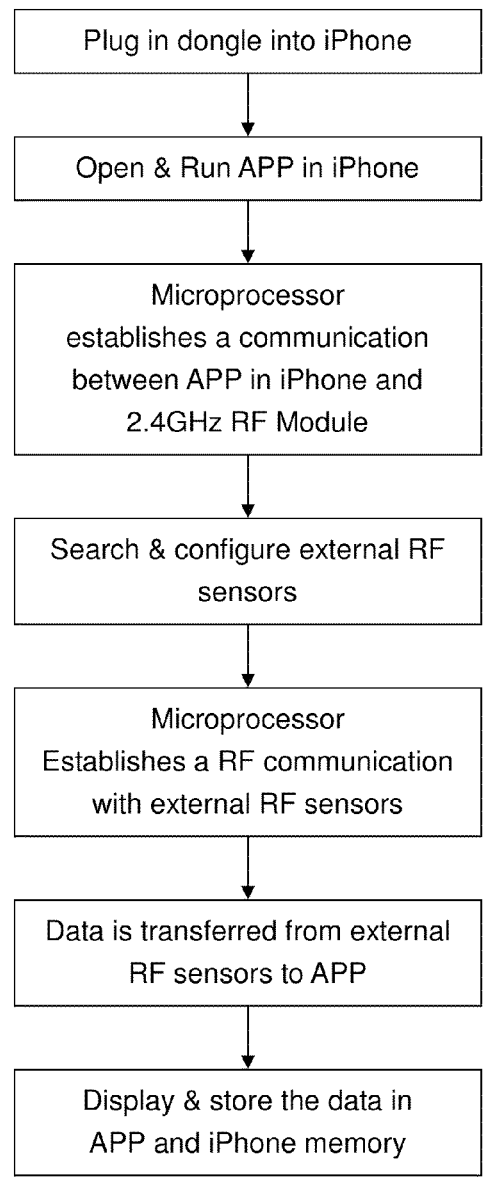
FIG. 10 is a flowchart depicting an exemplary operation flow of the bicycle computer apparatus of the present invention.

In operation, the user can operate the assembly by touching the transparent screen The second embodiment of the assembly 800 as shown in FIGS. 9 to 9B is substantially identical to that of FIG. 8, although a modified adapter pad is provided to fit a different shaped smart phone.

Figure 11:
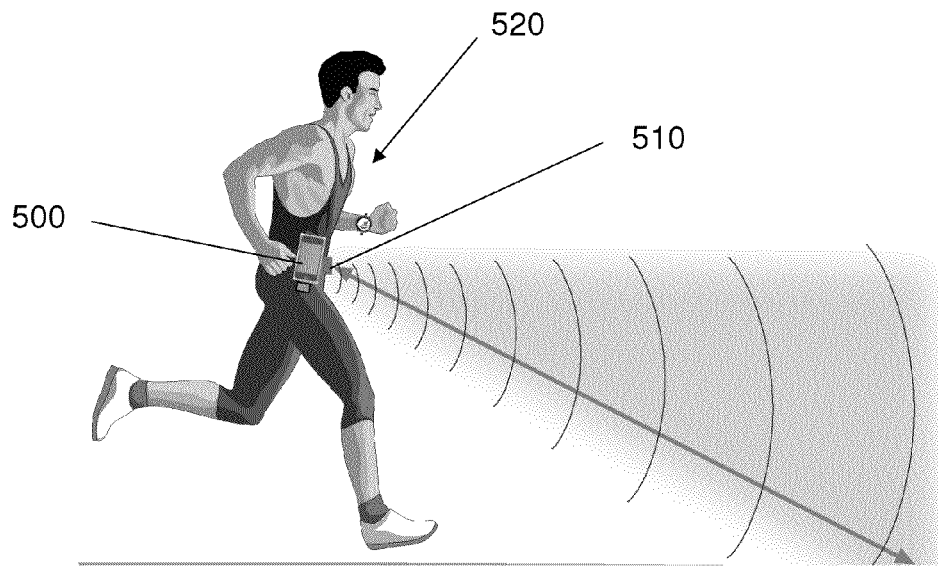
FIG. 11 depicts another embodiment of a sports performance monitor in another exemplary application.
Figure 12:
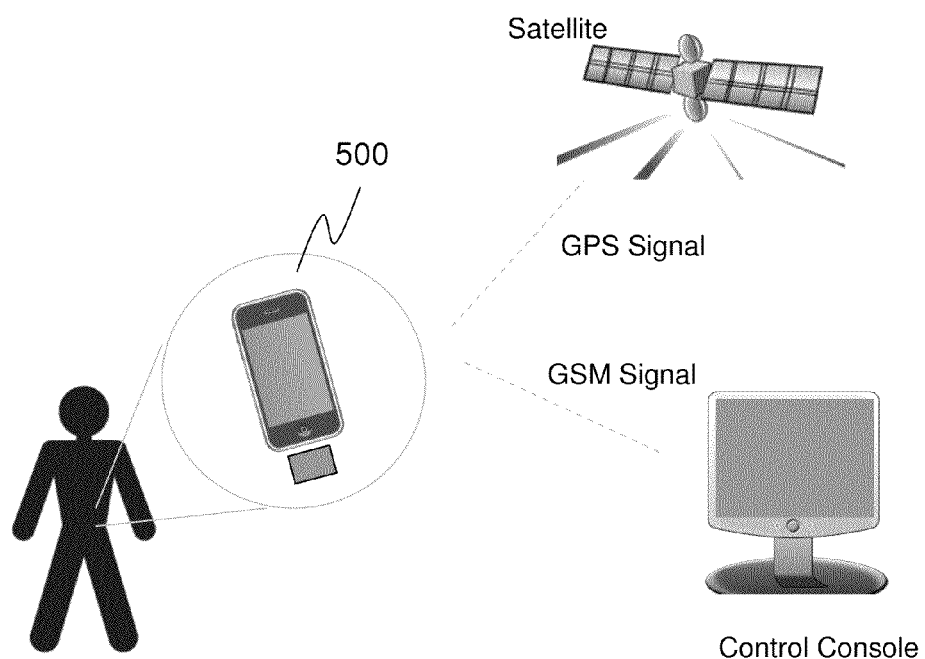
FIG. 12 is a schematic diagram illustrating an exemplary network application of the sports performance monitor of FIG. 10.

FIGS. 11 and 12 illustrate a runner's computer illustrating a second aspect of the present invention of a performance monitor. The runner's computer 500 comprises a smart phone and a runner's computer dongle. The runner's computer is substantially identical to that of the bicycle computer dongle 100 except that the microprocessor is adapted for monitoring running, such as step span, step frequency, step cadence, speed, and/or etc and the sensors are appropriated selected for that purposes. For example, a surface condition sensor 510 such as a sonar or radar, and a chest strap 520 comprising a heart rate sensor or ECG sensor are worn by runner. Similar to the bicycle computer, processing and telecommunications power of the smart phone is tapped to facilitate a more powerful running computer based on a dongle comprising a low-end cheap microprocessor to facilitate GPS, satellite, 2G to 4G, GSM or CDMA communications capability without loss of generality.

| Table of Numerals | |
|---|---|
| 100 | Bicycle computer dongle |
| 110 | Signal receiver |
| 112 | Antenna |
| 114 | RF receiver |
| 120 | Micro-processor |
| 130 | Adaptor |
| 140 | Housing |
| 150 | Display screen |
| 160 | Mobile phone |
| 170 | Display screen |
| 180 | Application program |
| 190 | Bicycle |
| 192 | Speed sensor |

Table of Numerals

| | | |
|---|---|---|
| | 194 | Power sensor |
| | 196 | Cadence sensor |
| | 198 | Heart-rate sensor |
| 200 | | Bicycle computer |
| 300 | | Bicycle computer pack |
| | 310 | Upper casing |
| | 312 | First receptacle |
| | 314 | Second receptacle |
| | 316 | Inter-receptacle aperture |
| | 318 | Bridge member |
| | 320 | Lower casing |
| | 322 | Resilient sealing ring |
| | 324 | Transparent window |
| | 330 | Movable clasps |
| | 340 | Adaptor pad |
| | 350 | Bicycle mounting bracket |
| | 360 | Closure tap |
| | 370 | Closure tap |
| 400 | | Bicycle computer dongle |
| 500 | | Runner's computer |
| | 510 | Condition sensor |
| | 520 | Chest strap |
| 800 | | Second embodiment of bicycle computer pack |

The invention claimed is:

1. A performance monitoring apparatus comprising:
an assembly of a performance monitoring module and a general purpose portable telecommunications device which are connected for data communication and a common casing to receive said assembly,
wherein the performance monitoring module is configured to receive performance signals from at least one performance sensor and to convert the performance signals into performance data, wherein the general purpose portable telecommunications device is configured to be activate-able to cause the performance monitoring module to transfer performance data to the general purpose portable telecommunications device,
wherein the common casing comprises mounting means for mounting said assembly onto sports equipment or a user,
wherein the common casing comprises a first receptacle for receiving the performance monitoring module and a second receptacle for receiving the portable telecommunications device, and the first and second receptacles are in communication via an inter-receptacle aperture defined by a bridge member on the common casing, and
wherein the bridge member is arranged also to latch the assembly of the performance monitoring module and the general purpose portable telecommunications device on the common casing.

2. A performance monitoring apparatus according to claim 1, wherein the performance monitoring module and the general purpose portable telecommunications device are mechanically connected in a mating relationship, and the common casing securely receives said assembly with said performance monitoring module and said general purpose portable telecommunications device in mechanically mated connection.

3. A performance monitoring apparatus according to claim 1, wherein the performance monitoring module comprises a protruding mechanical adapter for making a mating connection with the portable telecommunications device, and wherein the mechanical adapter extends through the inter-receptacle aperture when the performance monitoring module is seated in the first receptacle.

4. A performance monitoring apparatus according to claim 3, wherein the protruding mechanical adapter is received in the inter-receptacle aperture in a closely-fitted manner.

5. A performance monitoring apparatus according to claim 1, wherein the common casing is a reclose-able waterproof or watertight casing.

6. A performance monitoring apparatus according to claim 5, wherein the common casing further comprises a resilient adapter seat which is shaped to squarely seat the portable telecommunication in the second receptacle.

7. A performance monitoring apparatus according to claim 6, wherein the adapter seat is detachable so that different adapters are usable for seating different models of portable telecommunications devices in the second receptacle.

8. A performance monitoring apparatus according to claim 5, wherein the common casing is waterproof, with first and second receptacles individually sealed for water tightness.

9. A performance monitoring apparatus according to claim 5, wherein the common casing comprises a first moulded casing part on which the first and second receptacles are moulded and a second moulded casing part comprising a transparent window; wherein the second casing part is detachably attachable to the first moulded casing part by a clamping means, and forms a watertight enclosure enclosing the performance monitoring apparatus upon clamping.

10. A performance monitoring apparatus according to claim 1, wherein the performance monitoring module is a bicycle computer module.

11. A portable casing for receiving a performance monitoring apparatus, the performance monitoring apparatus comprising:
an assembly including a performance monitoring module and a general purpose portable telecommunications device which are connected for data communication,
wherein the performance monitoring module is configured to receive performance signals from at least one performance sensor and to convert the performance signals into performance data,
wherein the general purpose portable telecommunications device is configured to be activate-able to cause the performance monitoring module to transfer performance data to the general purpose portable telecommunications device,
wherein the portable casing is configured to securely receive said assembly with said performance monitoring module and said general purpose portable telecommunications device in mechanically mated connection and comprises a bicycle mounting means for mounting onto a bicycle,
wherein the casing comprises a first receptacle for receiving the performance monitoring module and a second receptacle for receiving the portable telecommunications device, and the first and second receptacles are in communication via an inter-receptacle aperture defined by a bridge member on the common casing, and
wherein the bridge member is arranged also to latch the assembly of the performance monitoring module and the general purpose portable telecommunications device on the common casing.

12. A portable casing according to claim 11, wherein the casing comprises a first moulded casing part on which the first and second receptacles are moulded and a second moulded casing part comprising a transparent window; wherein the second casing part is detachably attachable to the first moulded casing part by a clamping means, and forms a watertight enclosure enclosing the performance monitoring apparatus upon clamping.

13. A portable casing according to claim 11, wherein the casing comprises a first moulded casing part on which the first and second receptacles are moulded and a second moulded casing part comprising a transparent window; wherein the second casing part is detachably attachable to the first moulded casing part by a clamping means, and forms a watertight enclosure enclosing the performance monitoring apparatus upon clamping.

* * * * *